(12) United States Patent
Høyvik et al.

(10) Patent No.: US 7,156,906 B2
(45) Date of Patent: Jan. 2, 2007

(54) IMPREGNATING AGENT

(75) Inventors: Henrik Høyvik, Skien (NO); Liv Kari Sivertsen, Porsgrunn (NO)

(73) Assignee: Yara International ASA, Oslo (NO)

( * ) Notice: Subject to any disclaimer, the term of this patent is extended or adjusted under 35 U.S.C. 154(b) by 118 days.

(21) Appl. No.: 10/467,888

(22) PCT Filed: Feb. 13, 2002

(86) PCT No.: PCT/NO02/00062

§ 371 (c)(1),
(2), (4) Date: Aug. 29, 2003

(87) PCT Pub. No.: WO02/064336

PCT Pub. Date: Aug. 22, 2002

(65) Prior Publication Data

US 2005/0070438 A1    Mar. 31, 2005

(30) Foreign Application Priority Data

Feb. 13, 2001   (NO) .................................. 20010727

(51) Int. Cl.
*A01N 37/00* (2006.01)
*A01N 47/10* (2006.01)
*B27K 3/36* (2006.01)
*B27K 3/38* (2006.01)
*B27K 3/50* (2006.01)

(52) U.S. Cl. ................. 106/15.05; 106/18; 427/440; 514/557

(58) Field of Classification Search ............. 106/15.05, 106/18; 514/557; 427/440
See application file for complete search history.

(56) References Cited

U.S. PATENT DOCUMENTS

| | | | | |
|---|---|---|---|---|
| 5,468,892 A | * | 11/1995 | de Riese-Meyer et al. | 556/171 |
| 5,935,625 A | * | 8/1999 | Hjornevik et al. | 426/74 |
| 6,132,796 A | * | 10/2000 | Johnsen et al. | 426/643 |
| 6,137,005 A | * | 10/2000 | Hjornevik | 562/609 |
| 6,506,795 B1 | | 1/2003 | Barth et al. | 514/494 |
| 2004/0029961 A1 | * | 2/2004 | Von Krosigk et al. | 514/494 |
| 2004/0042929 A1 | * | 3/2004 | Von Krosigk et al. | 422/40 |
| 2004/0048747 A1 | * | 3/2004 | Netland et al. | 504/142 |

FOREIGN PATENT DOCUMENTS

| | | |
|---|---|---|
| EP | 0 739 698 | 7/2001 |
| GB | 1505388 | 3/1978 |
| GB | 1 542 390 | 3/1979 |
| JP | 55-77507 | 6/1980 |
| JP | 63-199604 | 8/1988 |
| PL | 90874 | 6/1977 |

OTHER PUBLICATIONS

WPI/Derwent's abstract, Accession No. 1980-52461C, week 8025, Abstract of JP, 55077507 (Andrews Shokai KK), Jun. 11, 1998.
WPI/Derwent's Abstract, Accession No. 1988-274240, week 8814, Abstract of JP, 63199604 (Daikinkogyc KK), Aug. 18, 1988.

* cited by examiner

*Primary Examiner*—Anthony Green
(74) *Attorney, Agent, or Firm*—Wenderoth, Lind & Ponack, L.L.P.

(57) ABSTRACT

The present invention relates to an impregnating agent for wood against fungi which will break down the cellulose and lignin in the wood. The impregnating agent comprises a mixture of potassium diformate and propionic- and/or acetic- and/or benzoic acid and/or a fixating agent. Said impregnating agent may comprise 0.5–5 weight % of the fixating agent selected among fatty acids, polymers and formates other than potassium diformate.

14 Claims, 8 Drawing Sheets

IMPREGNATING AGENT

The present invention relates to an impregnating agent and its use against fungi which will break down the cellulose and lignin in wood.

A small group of fungi are especially effective in breaking down cellulose and lignin, hardly any other group of organism is capable of doing this. There are two main explanations for this. Firstly, cellulose is a solid substance which the cells can not include in themselves and break down. Secondly, cellulose is macro-molecular, composed of only glucose units by means of strong β-1.4 glucosidic bindings. The cellulose splitting fungi have solved this problem by liberating extra cellular enzymes which will break down the cellulose molecule, finally all the way down to glucose which can be methabolized. Outdoor paints and varnishes depend heavily on fungicides which go into the wood and prevent that the cellulose molecule is broken down.

Impregnation of wood to solve the above problems was previously solved by application of rather toxic agents like arsenic-, chromium- and copper based salts, but use of these are limited today due to their negative effect on the environment. Today it is mainly organic fungicides which are used. Another problem in finding suitable impregnating agents is that they should not be too easily solvable in water and thereby being rapidly washed out.

There are known numerous impregnating agents which at least partly solves the problems, but ever stricter environmental regulations and demand for more cost effective products requires new solutions. Examples of known impregnating agents are:

EP-739698 relating to a wood preservative comprising 1–35 weight % of a product obtained by mixing 25–75 weight % of an ethoxylated fatty amine and 75–25 weight % of a 3–25C unsaturated fatty acid or its Cu and/or Zn salts. This chromium free wood impregnating agent is stated to not have the leaching problems of prior art Cr-free compositions.

GB-1,542,390 relating to an impregnating agent for protecting wood against blue stain. Said agent is an alkaline-reacting preservative composition comprising 6–11C normal fatty acids and/or HF and NaOH, $Na_2CO_3$, KOH or $K_2CO_3$. The composition is readily soluble in water, and health problems and fire risks associated with the use of organic solvents are avoided. Further, it is known from JP-55077507 a wood preservative composition comprising essentially boric acid (15–25%), sodium fluoride (30–40%), zinc formate or copper formate (5–15%) and copper or zinc acetate (5–15%), optionally mixed with triethanolamine as a reaction controlling agent.

The main object of the invention was to arrive at an impregnating agent that would be environmentally acceptable and still prevent fungi from breaking down or degrading the cellulose and lignin molecules of the wood.

Another object was to arrive at an impregnating agent that would function over a prolonged time and not be easily washed out during storage of treated wood.

It was a further object to arrive at an agent that was compatible and could function together with paints and lacquers.

Though it is desired that the impregnating agent has a low solubility in water in order to avoid that it is washed out, the inventors started to look for water soluble agents that would not harm the environment. Thus toxic solvents were excluded. The problem could of course then be how to prevent the impregnating agent from being washed out. Lower monocarboxylic acids have been used for a long time in silage of grass and are accepted from an environmental point of view. However, even if they should have some effect on the fungi in question, they would obviously be washed out of the wood very rapidly. Accordingly, these acids were initially ruled out as useless. The inventors then started to test some of the salts of such acids. It was then found that potassium diformate had surprisingly good effect against the fungi that were known to be damaging to wood. But the effect proved to last for a short time if the impregnated wood was exposed to water which soon washed out the impregnating agent. In spite of the shortcomings of this agent the experiments were followed up by mixing the potassium diformate with various monocarboxylic acids, and it was found that mixtures of potassium diformate and propionic- and/or benzoic- and/or acetic acid were more effective against the fungi and remained longer in the wood when it was exposed to water. Thus the total impregnating effect was found to be most interesting. The new impregnating agent would not cause any serious damage to the environment during treatment of the wood or later use of such impregnated wood.

The impregnating agent could be further improved by adding various fixating agents. Also the fixating agents should be environmentally acceptable even if they are applied in small amounts. Useful fixating agents could be fatty acids, preferably $C_{18}$–$C_{22}$ fatty acids, polymers as starch, cellulose and chitosan and even other formates like ammonium tetraformate, calcium formate, copper formate etc. Foam depressing agents may, if necessary, be added to the impregnating agent.

The impregnating agent according to the invention comprises a mixture of potassium diformate and propionic- and/or acetic- and/or benzoic acid and/or a fixating agent.

The impregnating agent may comprise 40–60 weight % of the aqueous potassium diformate solution and 60–40 weight % of the aqueous solution of said acids.

The impregnating agent may comprise a mixture of a 30–60 weight % aqueous solution of potassium diformate and a 10–20 weight % aqueous solution of propionic acid.

The impregnating agent may comprise a mixture of 40–50 weight % aqueous solution of potassium diformate and a 15–20 weight % aqueous solution of propionic acid.

The impregnating agent may comprise a mixture of potassium diformate and a fixating agent.

The amount of fixating agent may be 0.5–5 weight %, and the agent may be selected among fatty acids, polymers and other formates, preferably selected among $C_{18}$–$C_{22}$ fatty acids, starch, cellulose and chitosan.

The impregnating agent may also be used for surface treatment of wood.

The invention is further explained and envisaged in the following figures and examples:

EXAMPLE 1

This example shows the effect of treatment with a 50 weight % potassium diformate on two test organisms, i.e. *Coniophora puteana* and *Dacrymyces stillatus*, the former is a standard organism in such tests prescribed for use in the European Standard Test EN 113.

The tests were carried out in the following way:

Small blocks of wood of the prescribed size 5 cm×2.5 cm×1.5 cm were numbered and then dried in an oven at 105° C. for 24 hours, cooled and weighed. That represented the dry weight at start. The test block had a start weight between 7.5–9.5 grams. The blocks were impregnated with said solution and control blocks with sterile distilled water under vacuum for 10 minutes and then left in the impregnating solution for 1 hour, whereupon they were completely soaked with the impregnating solution. Subsequent to this impregnation the blocks were placed on filter paper for 30 minutes for drainage. The test blocks were then washed three times with distilled water for 2 minutes and then left in distilled water for 24 hours and finally washed three times with distilled water and then placed on filter paper for drainage. Four blocks were used for each concentration of impregnating solution with 2 blocks in each test flask, so-called Kolle flasks. The duration of the tests was 3 months. The blocks were then removed from the flasks and scraped clean of fungi, whereupon they were dried at 105° C. for 24 hours and weighed and percent reduction in dry weight was calculated. The results of these experiments are shown in FIGS. 1, 2, 3 and 4. Further experiments showed that propionic acid could be substituted with acetic and/or benzoic acid.

Figure 1:
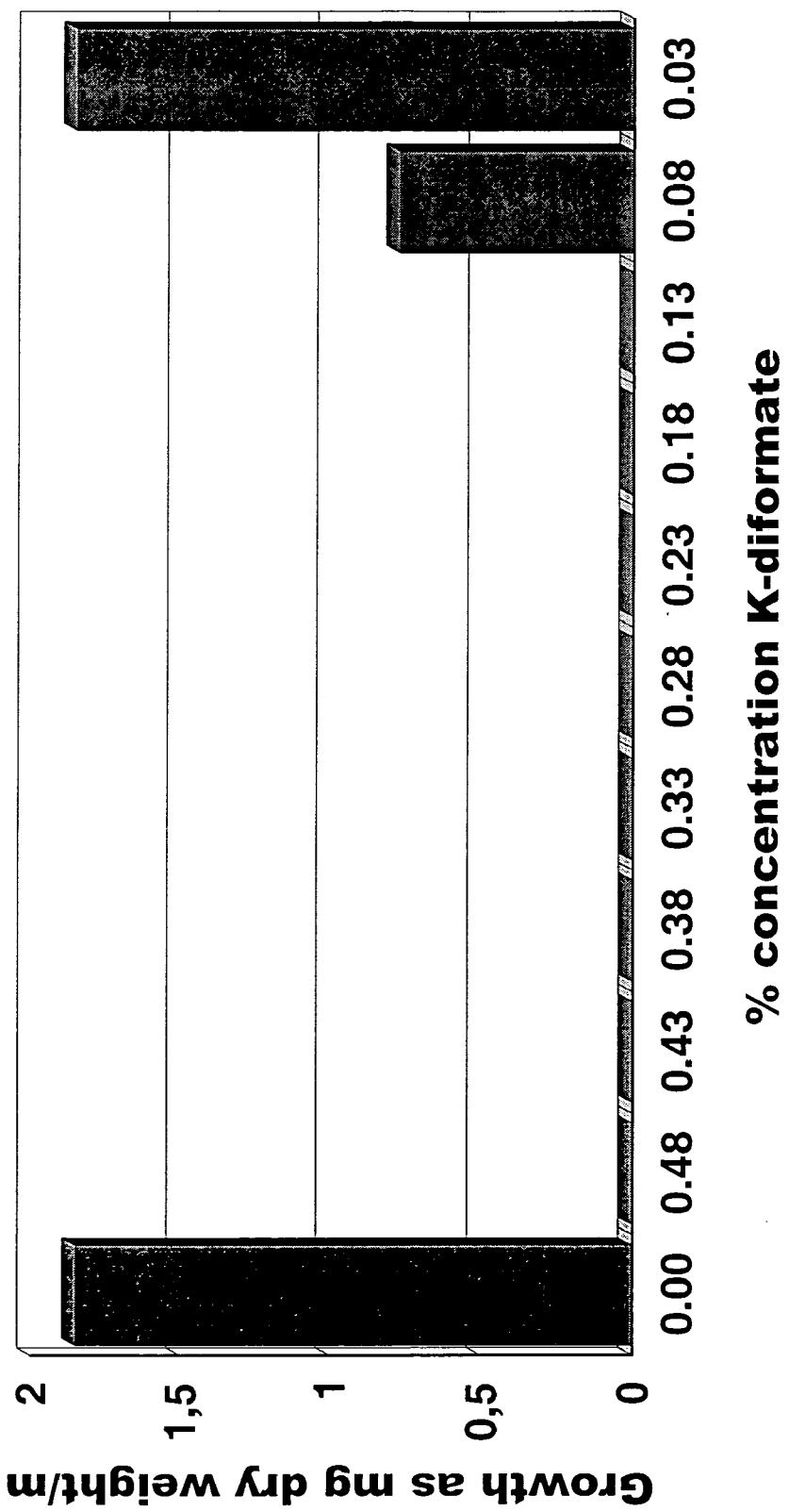
FIG. 1 shows growth of the fungi *Coniophora puteana* at varying concentrations of K-diformate.
Figure 2:
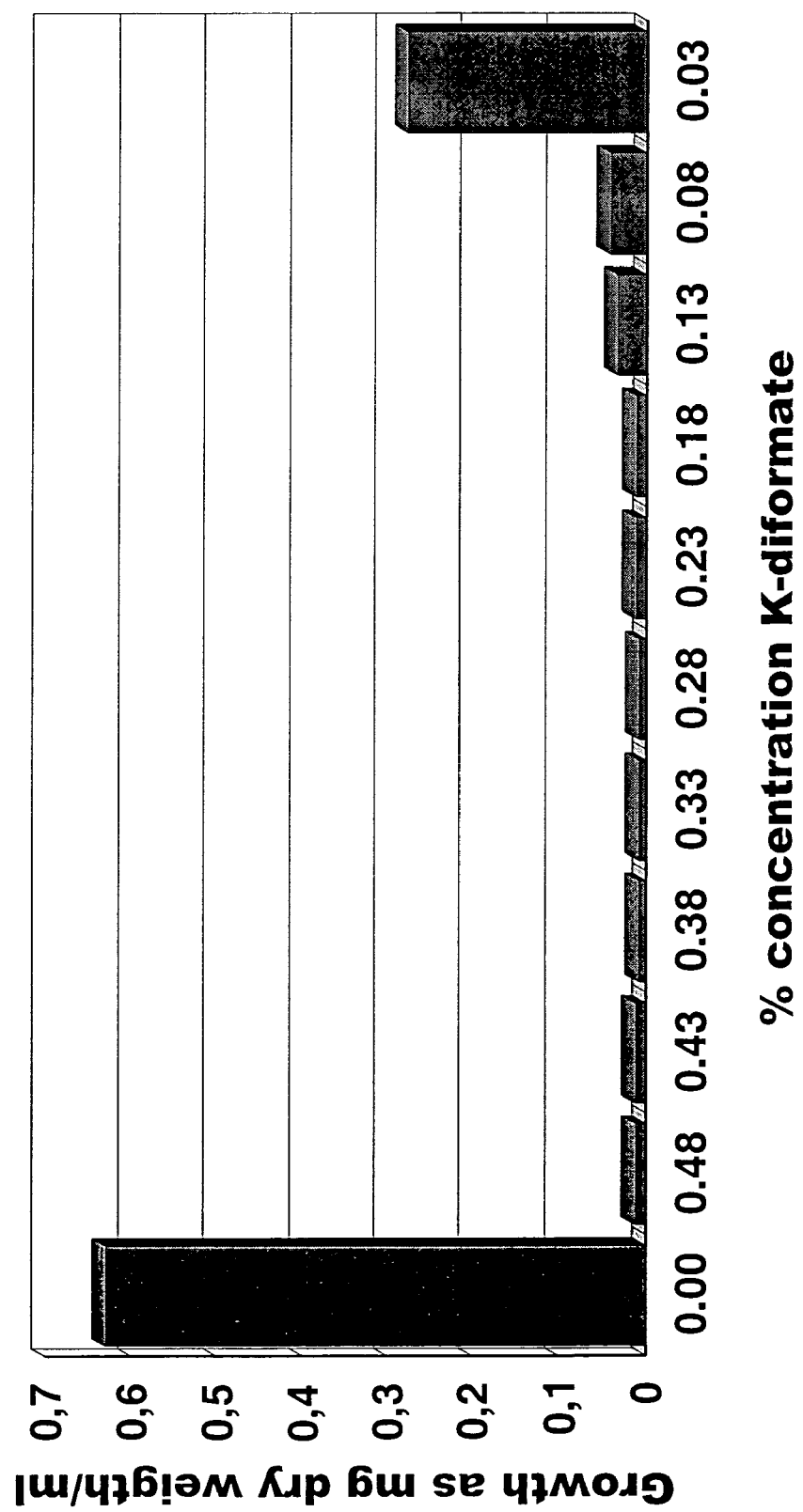
FIG. 2 shows growth of the fungi *Dacrymyces stillatus* at varying concentrations of K-diformate.
Figure 3:
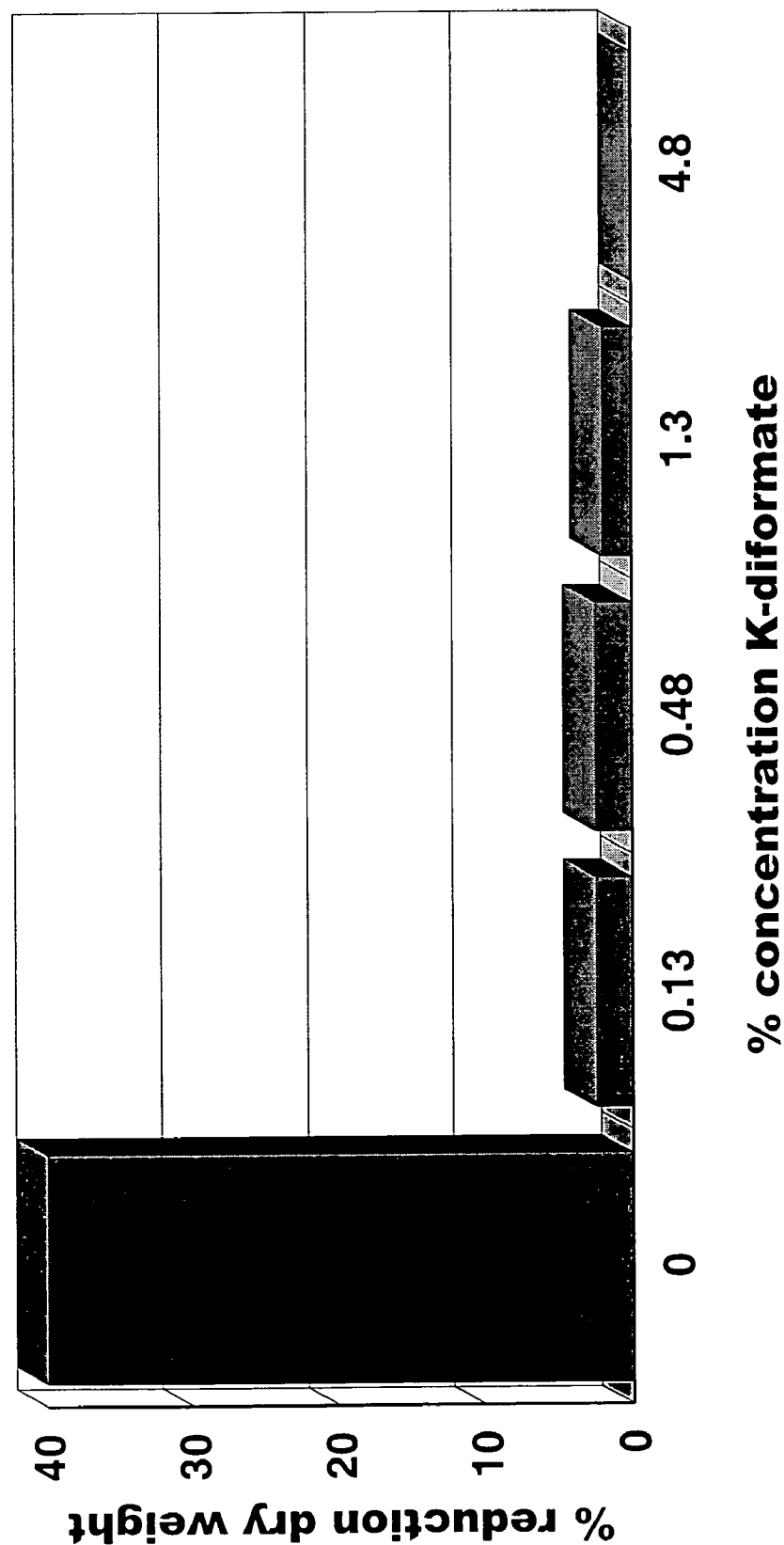
FIG. 3 shows % reduction of dry matter for the fungi *Coniophora puteana* using K-diformate, and without subsequent washing.
Figure 4:
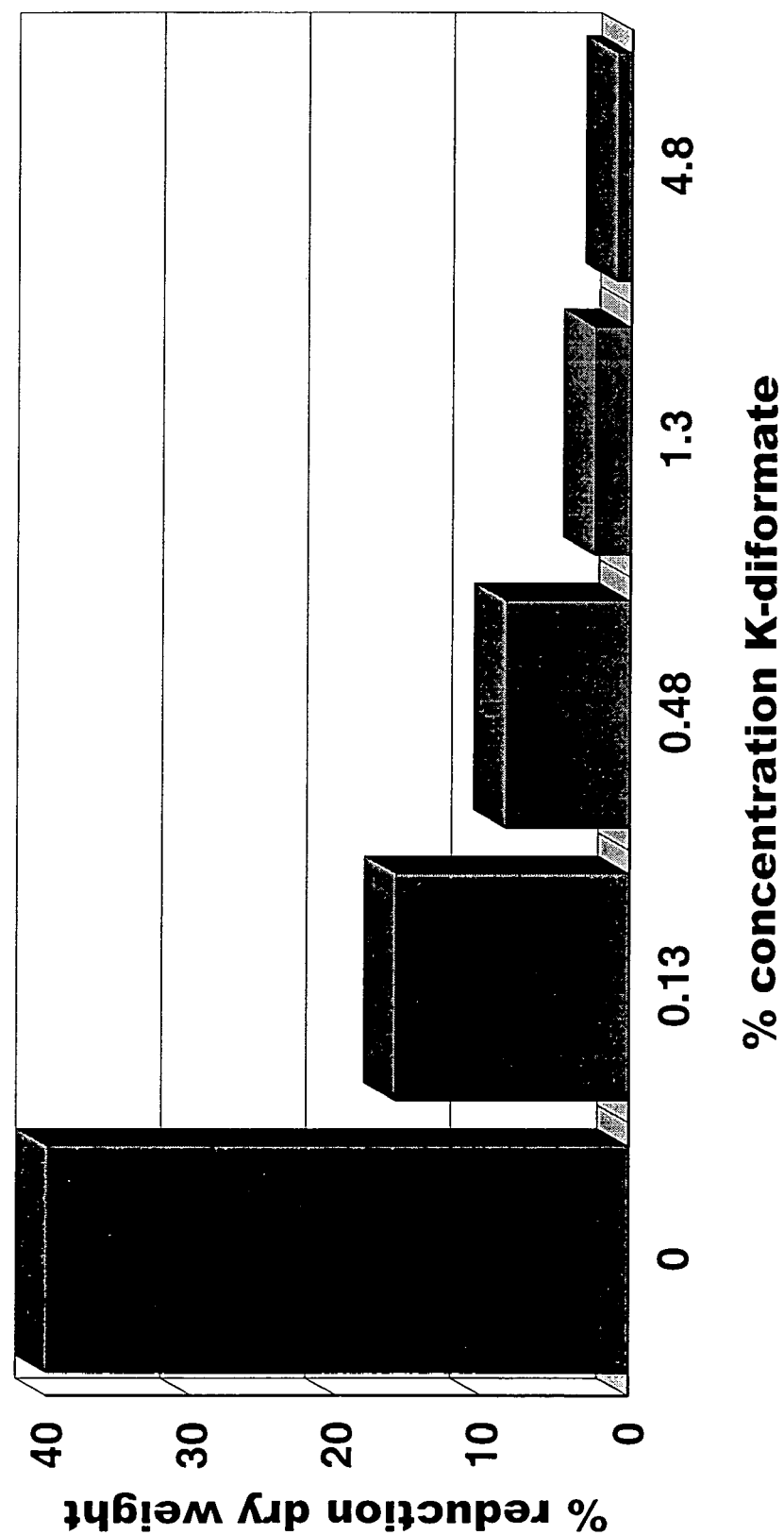
FIG. 4 shows % reduction of dry matter for the fungi *Coniophora puteana* using K-diformate, and with subsequent washing.

FIG. 1 shows that for the fungi *Coniophora puteana* potassium diformate will act as an effective fungicide provided it is applied in concentrations of at least 0.13 weight %. Also for the fungi *Dacrymyces stillatus* potassium diformate has some fungicidal effect, but for these fungi it is necessary to use at least 0.18 weight % K-diformate to achieve complete retardation in growth. The effect and applicability of K-diformate are more clearly demonstrated by FIGS. 3 and 4 showing reduction of dry matter after exposure with the fungi *Coniophora puteana* applying K-diformate with and without subsequent washing of the test blocks. Firstly, the figures show that the control with distilled water gives a reduction in dry matter of almost 40%. Complete effect of K-diformate was attained with 1.3–2%. However, as shown by FIG. 4 the fungicidal effect of K-diformate decreases very rapidly when the test blocks are exposed to water and it will be necessary to use as much as 4.8% K-diformate to obtain required effect and this amount is almost prohibitive.

EXAMPLE 2

This example shows the fungicidal effect of an impregnating agent comprising a 50—50% mixture of K-diformate solution and propionic acid. The tests were performed as in Example 1 and on the same fungi. The results of the experiments are shown in FIGS. 5–8.

Figure 5:
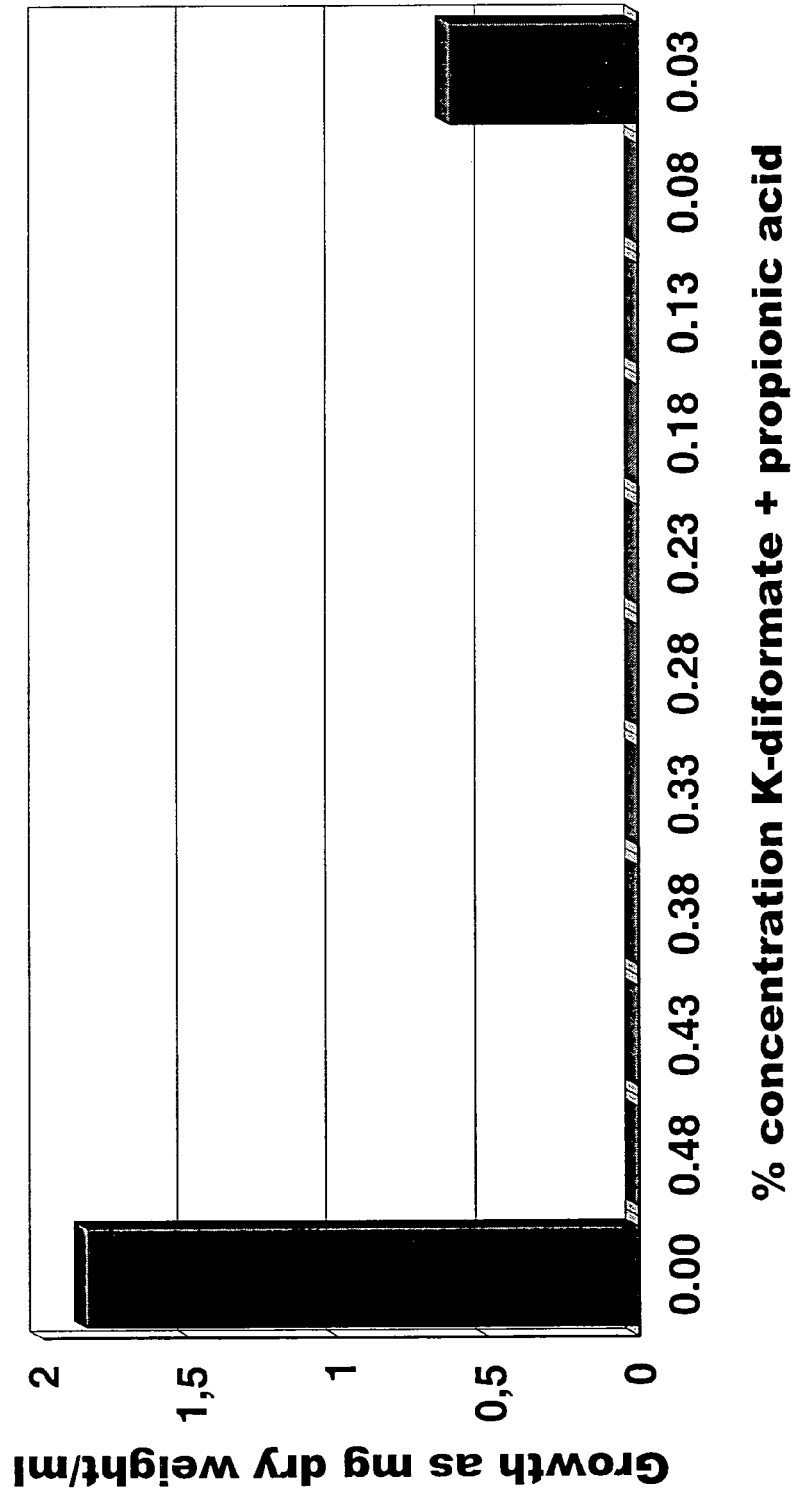
FIG. 5 shows growth of the fungi *Coniophora puteana* at varying concentrations using an impregnating agent according to the invention.
Figure 6:
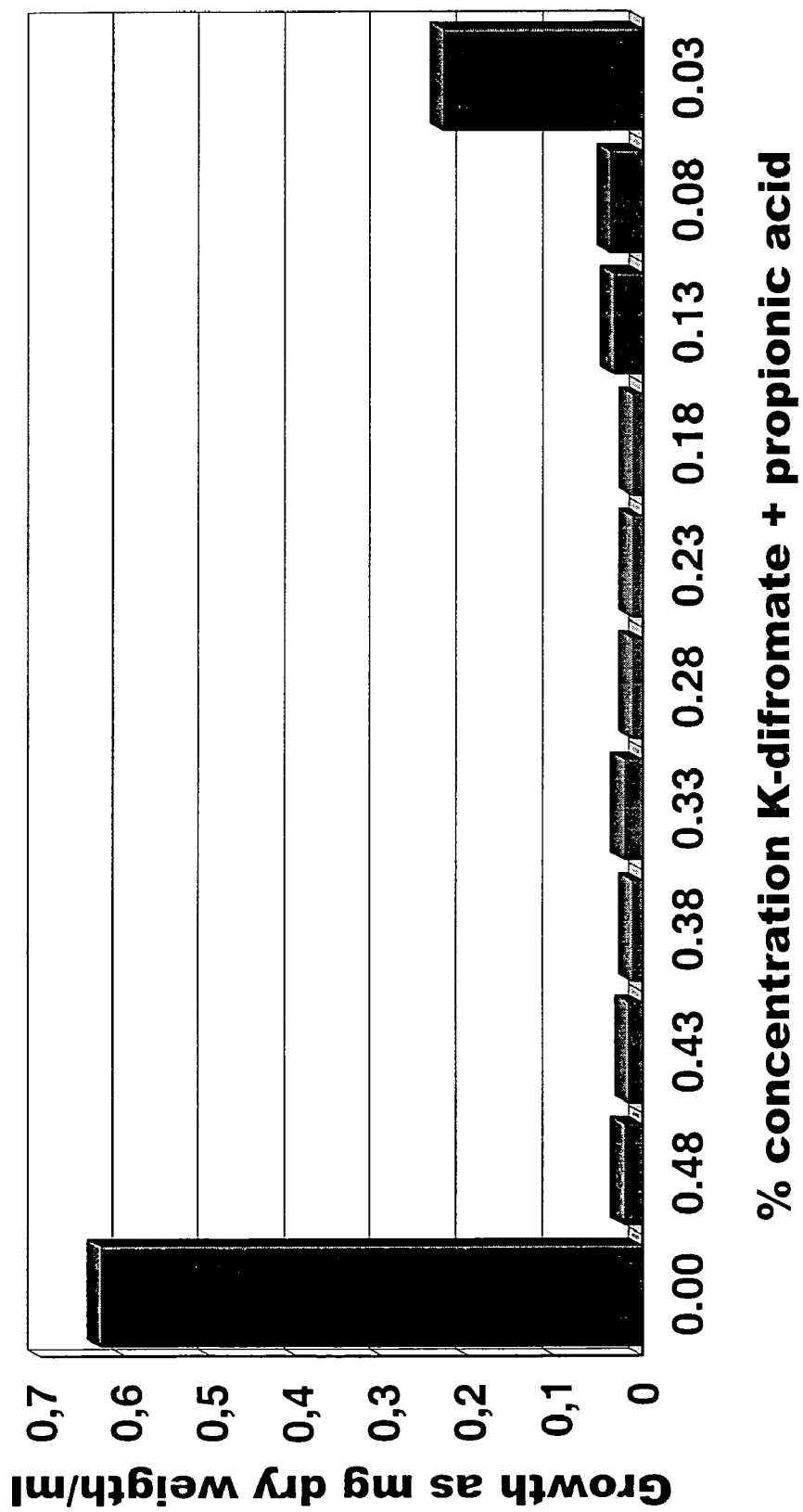
FIG. 6 shows growth of the fungi *Dacrymyces stillatus* at varying concentrations using an impregnating agent according to the invention.
Figure 7:
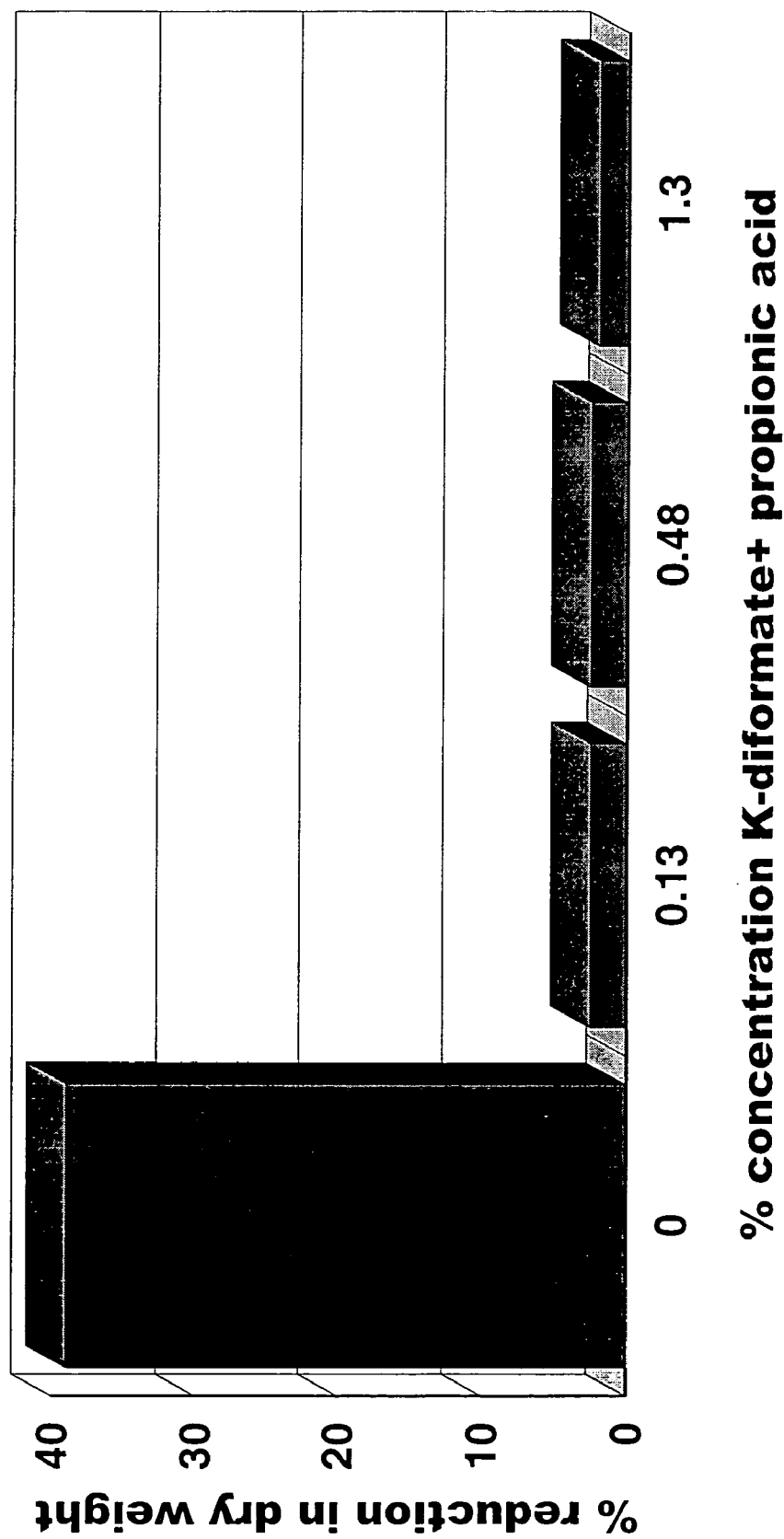
FIG. 7 shows % reduction of dry matter for the fungi *Coniophora puteana* using an impregnating agent according to the invention, and without subsequent washing.
Figure 8:
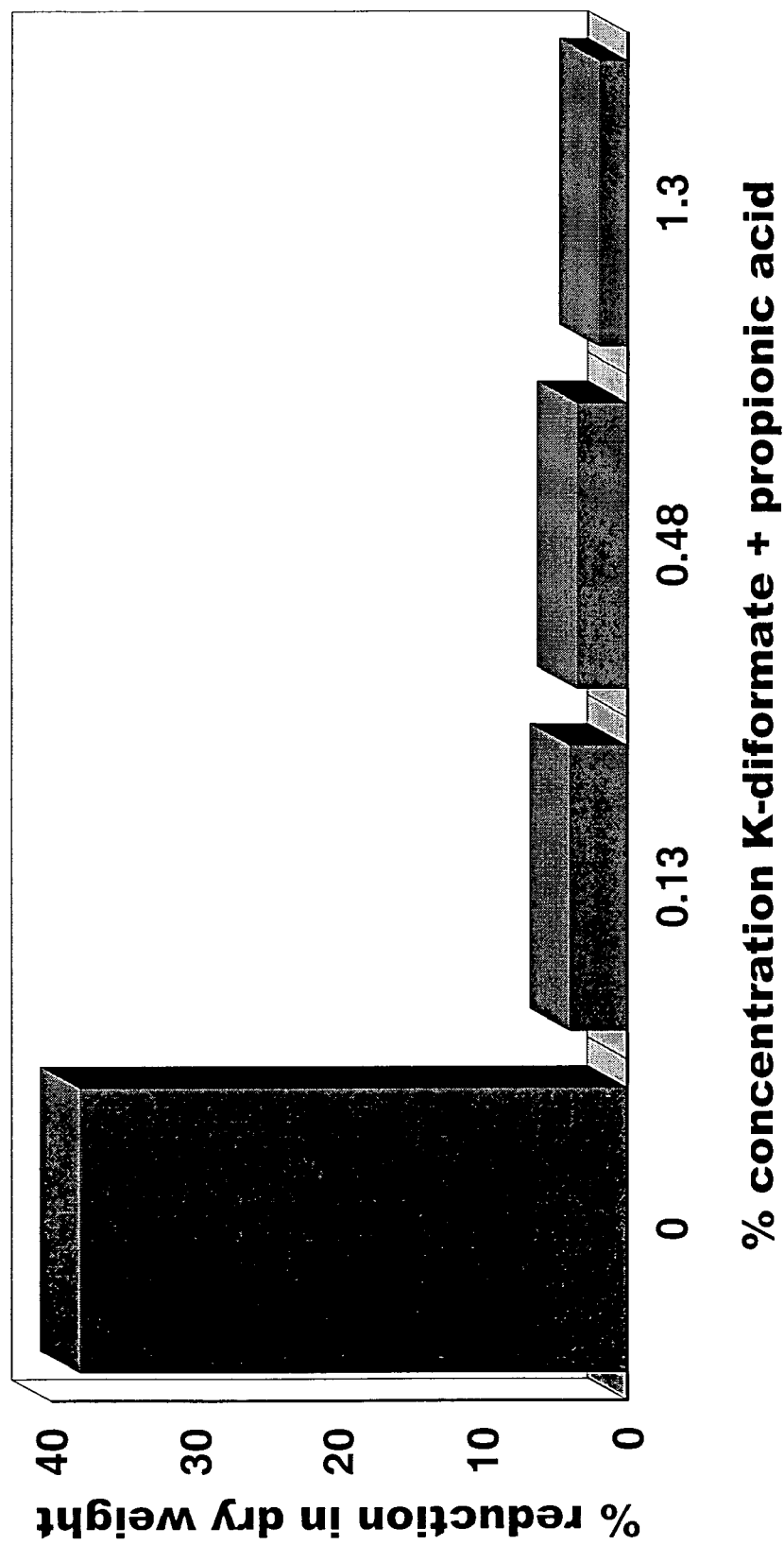
FIG. 8 shows % reduction of dry matter for the fungi *Coniophora puteana* using an impregnating agent according to the invention, and with subseqent washing.

FIG. 5 shows that with regard to the fungi *Coniophora puteana* the above impregnating mixture is more effective than K-diformate alone as only 0.08% of the mixture is necessary for obtaining the same effect as for K-diformate. With regard to the fungi *Dacrymyces stillatus* the difference in effect is not equally dominant. The FIGS. 7 and 8 show the reduction in dry matter after exposure to the fungi *Coniophora puteana*. The above mixture of K-diformate and a mono-carboxylic acid was applied during the experiments. Without subsequent washing the effect is most acceptable as 0.13% seems to be 100% retarding to growth. The results subsequent to washing (FIG. 8) show that the effect is slightly lower. Keeping in mind that said salt-acid mixture is highly soluble in water, the conclusion will be that K-diformate+propionic acid, even after washing, have a very good fungicidal effect.

EXAMPLE 3

This example shows the effect of adding different fixation agents to an impregnating agent comprising 42.5% K-diformate and 15% propionic acid (A) and to another impregnating agent comprising 65% ammonium tetraformate and 10% propionic acid and 2% benzoic acid (B).

The following products were tested:

Product 1:42.5% K-diformate+15% propionic acid (A).
Product 2:65% Ammonium tetraformate+10% propionic acid+2% benzoic acid (B).
Product 3: Aqueous solution of (2% A+2% $C_{18}$–$C_{22}$ fatty acids).
Product 4: Aqueous solution of (2% B+2% $C_{18}$–$C_{22}$ fatty acids).
Product 5:2% aqueous solution of (A+5% starch).
Product 6:2% aqueous solution of (A+1% cellulose).
Product 7:2% aqueous solution of (A+0.5% chitosan).
Product 8:2% aqueous solution of (A+1.3% Cu-formate).

Small blocks of wood of the prescribed size 5 cm×2.5 cm×1.5 cm were prepared and the impregnating liquid was fixated in the wood in accordance with European Standard Test EN 113 (1997). The leaching procedure comprising impregnation with water and immersion in water of the wood blocks was done according to European Standard Test EN 84 (1997). The water was changed nine times during the immersion period, and the water at the end of the first and second day of immersion and the water from the impregnation were analysed together. The water from the remaining seven changes was also collected and analysed. From said analyses of the washing water and impregnation water the total amount of leakage is found simply by adding the results. K-diformate is present in water as $HCOO^-$ and $K^+$, so the amount of formate in the water was measured and from that value the amount of K-diformate which had leaked out of the wood was calculated.

The results of the experiment are shown in Table 1.

Formate mg: Total amount of formate in the collected water.
K-diformate mg: Calculated amount of K-diformate leaked out of the wood blocks.
Theoretical K-diformate mg: Theoretical amount of K-diformate impregnated in the wood blocks.
Propionate mg: Total amount of propionate in the collected water.
% leakage K-diformate=(K-diformate mg/Theoretical K-diformate mg)*100%
% leakage Propionate=(Propionate mg/Theoretical Propionate mg)*100%

TABLE 1

| Product | Formate mg | K-diformate mg | Theoretrical K-diformate mg | Propionate mg | Theoretical Propionate mg | % leakage K-diformate | % leakage Propionate |
| --- | --- | --- | --- | --- | --- | --- | --- |
| Product 1 | 23.2 | 32.7 | 188 | 26.4 | 66 | 17.4 | 40.0 |
| Product 2 | 13.1 | | | 20.6 | 44 | | 46.8 |
| Product 3 | 16.8 | 23.7 | 185 | 15.0 | 65 | 12.8 | 23.1 |
| Product 4 | 12.9 | | | 16.9 | 44 | | 38.4 |
| Product 5 | 15.9 | 22.5 | 194 | 23.9 | 68 | 12.9 | 35.1 |
| Product 6 | 13.8 | 19.5 | 190 | 20.0 | 67 | 10.3 | 29.8 |
| Product 7 | 13.1 | 18.5 | 197 | 18.7 | 69 | 9.4 | 27.1 |
| Product 8 | 16.3 | 23.1 | 194 | 22.8 | 69 | 11.9 | 33.0 |

This example shows that the addition of fatty acids or polymers have a positive effect on fixation, i.e. there is less leakage of the impregnating agent when adding the above fixation agents. In Table 1 the leakage values in the two last columns are clearly lower for products 3 to 8 which contain fixation agents than for products 1 and 2 without fixating agents.

From the above examples it can be seen that the inventors have succeeded in arriving at impregnating agents which are effective in relatively low concentrations and will function over a prolonged period of time. The new impregnating agent comprising a mixture of K-diformate and propionic- and/or acetic- and/or benzoic acid and/or a fixating agent is also environmentally friendly and in spite of its high solubility in water will be effective even after the wood has been exposed to water.

The invention claimed is:

1. An impregnating agent for wood against fungi which will break down cellulose and lignin in the wood, wherein the impregnating agent comprises 40–60 weight % of an aqueous potassium diformate solution and 60–40 weight% of an aqueous solution of propionic- and/or acetic- and/or benzoic acid.

2. An impregnating agent for wood against fungi which will break down cellulose and lignin in the wood, wherein the impregnating agent comprises a mixture of a 30–60 weight % aqueous solution of potassium diformate and a 10–20 weight % aqueous solution of propionic acid.

3. The impregnating agent according to claim 2, which comprises a mixture of a 40–50 weight % aqueous solution of potassium diformate and a 15–20 weight % aqueous solution of propionic acid.

4. The impregnating agent according to claim 1, which further comprises a fixating agent selected from the group consisting of fatty acids, polymers and copper formate.

5. The impregnating agent according to claim 4, which contains 0.5–5 weight % of the fixating agent.

6. The impregnating agent according to claim 4, wherein the fixating agent is selected from the group consisting of $C_{18}$–$C_{22}$ fatty acids, starch, cellulose and chitosan.

7. The impregnating agent according to claim 2, which further comprises a fixating agent selected from the group consisting of fatty acids, polymers and copper formate.

8. A method of treating wood which comprises impregnating the wood with an impregnating agent for wood against fungi which will break down cellulose and lignin in the wood, wherein the impregnating agent comprises a solution comprising a mixture of potassium diformate and propionic- and/or acetic- and/or benzoic acid and/or a fixating agent selected from the group consisting of fatty acids, polymers and copper formate.

9. A method of treating wood which comprises impregnating the wood with the impregnating agent of claim 1.

10. A method of treating wood which comprises impregnating the wood with the impregnating agent of claim 2.

11. A method of treating wood which comprises impregnating the wood with the impregnating agent of claim 3.

12. A method of treating wood according to claim 8, wherein the impregnating agent comprises a mixture of potassium diformate and the fixating agent.

13. A method of treating wood according to claim 8, wherein the impregnating agent contains 0.5–5 weight % of the fixating agent.

14. A method of treating wood according to claim 8, wherein the fixating agent is selected from the group consisting of $C_{18}$–$C_{22}$ fatty acids, starch, cellulose and chitosan.

* * * * *